(12) United States Patent
Jong et al.

(10) Patent No.: US 11,561,270 B2
(45) Date of Patent: Jan. 24, 2023

(54) APPARATUS AND METHOD FOR NANO MAGNETIC PARTICLE IMAGING

(71) Applicant: ELECTRONICS AND TELECOMMUNICATIONS RESEARCH INSTITUTE, Daejeon (KR)

(72) Inventors: Jae-Chan Jong, Daejeon (KR); Seung-Min Choi, Daejeon (KR); Hyo-Bong Hong, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 267 days.

(21) Appl. No.: 16/939,983

(22) Filed: Jul. 27, 2020

(65) Prior Publication Data
US 2021/0059557 A1    Mar. 4, 2021

(30) Foreign Application Priority Data

Aug. 30, 2019  (KR) .................. 10-2019-0107261
May 22, 2020  (KR) .................. 10-2020-0061654

(51) Int. Cl.
    *G01R 33/12*    (2006.01)
    *G01R 33/34*    (2006.01)
    *A61B 5/0515*    (2021.01)

(52) U.S. Cl.
CPC ... *G01R 33/1276* (2013.01); *G01R 33/34053* (2013.01); *A61B 5/0515* (2013.01)

(58) Field of Classification Search
CPC .......... G01R 33/1276; G01R 33/34053; A61B 5/0515
See application file for complete search history.

(56) References Cited

U.S. PATENT DOCUMENTS

| 4,940,057 A * | 7/1990 | Kamei | ............... G01R 33/36 324/318 |
| 9,759,789 B2 | 9/2017 | Schmale | |

(Continued)

FOREIGN PATENT DOCUMENTS

| JP | 2015502213 A | 1/2015 |
| KR | 20090060143 A | 6/2009 |

(Continued)

OTHER PUBLICATIONS

Bernhard Gleich et al., "Tomographic imaging using the nonlinear response of magnetic particles," Nature, vol. 435, pp. 1214-1217, Jun. 30, 2005.

*Primary Examiner* — Dixomara Vargas

(57) ABSTRACT

Disclosed herein are an apparatus and method for imaging nano magnetic particles. The apparatus may include a measurement head in which a through hole for accommodating a sample including nano magnetic particles is formed and in which an excitation coil and a detection coil are installed, a field-free region generation unit for forming a field-free region, in which there are few or no magnetic fields, in a spacing area between the identical magnetic poles that face each other, and a control unit for applying a signal to the excitation coil when the measurement head is located inside the spacing area of the field-free region generation unit, controlling the field-free region so as to move in the sample, and imaging the 3D positional distribution of the nano magnetic particles included in the sample based on a detection signal output from the detection coil.

16 Claims, 11 Drawing Sheets

(56) References Cited

U.S. PATENT DOCUMENTS

| | | | |
|---|---|---|---|
| 10,261,141 B2* | 4/2019 | Tonyushkin | G01R 33/1276 |
| 10,267,867 B2 | 4/2019 | Choi et al. | |
| 10,267,873 B2* | 4/2019 | Gleich | G01R 33/28 |
| 10,650,555 B2 | 5/2020 | Chae et al. | |
| 11,194,385 B2* | 12/2021 | Chou | H04B 5/02 |
| 2008/0309330 A1* | 12/2008 | Ohyu | A61B 5/05 |
| | | | 324/232 |
| 2011/0196226 A1* | 8/2011 | Gross | A61N 5/1049 |
| | | | 600/411 |
| 2011/0255731 A1* | 10/2011 | Ball | B06B 1/045 |
| | | | 381/396 |
| 2012/0265050 A1* | 10/2012 | Wang | A61B 6/485 |
| | | | 600/407 |
| 2014/0113828 A1* | 4/2014 | Gilbert | H01F 6/06 |
| | | | 252/500 |
| 2014/0159712 A1* | 6/2014 | Graziani | A61B 5/0515 |
| | | | 324/232 |
| 2015/0244482 A1* | 8/2015 | Biber | G01R 33/3621 |
| | | | 370/480 |
| 2015/0260818 A1* | 9/2015 | Campagna | G01R 33/3621 |
| | | | 324/309 |
| 2015/0289939 A1* | 10/2015 | Rahmer | A61B 5/0515 |
| | | | 600/409 |
| 2017/0067730 A1 | 3/2017 | Hong et al. | |
| 2018/0085024 A1* | 3/2018 | Rosen | A61B 5/055 |
| 2018/0231629 A1* | 8/2018 | Top | A61B 5/0515 |
| 2018/0292481 A1* | 10/2018 | Niemann | G01N 24/08 |
| 2018/0335487 A1* | 11/2018 | Tonyushkin | A61B 5/0515 |
| 2019/0231191 A1* | 8/2019 | Hofmann | A61B 5/0035 |
| 2019/0317167 A1* | 10/2019 | Laborde | G01R 33/5601 |
| 2021/0405134 A1* | 12/2021 | Lim | G01R 33/1276 |
| 2022/0087564 A1* | 3/2022 | Kim | A61B 5/0046 |

FOREIGN PATENT DOCUMENTS

| | | |
|---|---|---|
| KR | 20110137510 A | 12/2011 |
| KR | 20180131914 A | 12/2018 |

* cited by examiner

APPARATUS AND METHOD FOR NANO MAGNETIC PARTICLE IMAGING

CROSS REFERENCE TO RELATED APPLICATIONS

This application claims the benefit of Korean Patent Applications No. 10-2019-0107261, filed Aug. 30, 2019, and No. 10-2020-0061654, filed May 22, 2020, which are hereby incorporated by reference in their entireties into this application.

BACKGROUND OF THE INVENTION

1. Technical Field

The disclosed embodiment relates generally to technology for imaging a specific object included in a sample, and more particularly to technology for imaging the spatial distribution of Nano Magnetic Particle (NMP) material.

2. Description of the Related Art

Magnetic Particle Imaging (MPI) devices using Nano Magnetic Particles (NMP) are being developed mainly in the U.S. and Europe as next-generation medical devices. Particularly, devices capable of acquiring images of small animals, such as mice, are being developed.

When compared with Magnetic Resonance Imaging (MRI) or X-ray scanning, which are most commonly used these days, MPI is advantageous in imaging a specific region corresponding to a lesion, such as a tumor, although it cannot be used to acquire anatomical images. Therefore, MPI is currently being researched and developed for multimodal medical imaging devices integrating the same with MRI or CT X-ray.

Meanwhile, Positron Emission Tomography (PET) has been known to date to be most useful to detect early signs of cancer or Alzheimer's disease, but is strictly regulated due to the use of a radioactive substance. Further, PET is of limited applicability because the range of types of tracers capable of being used as radiopharmaceuticals suitable for analysis of tissue or cells is limited.

Therefore, PET may be replaced with MPI. Moreover, MPI has an advantage in that it may be extensively used because it is theoretically possible to use more than hundreds of thousands of types of antigens and antibodies developed to date.

The basic principle of MPI devices, having been developed so far by Bruker & Philips Corporation in Europe or Magnetic Insight in the U.S., is to generate a magnetic-field-free region (Field-Free Line or Field-Free Point (hereinafter, 'FFL' or 'FFP')) and to acquire an image signal using the movement of the magnetic-field-free region. These MPI devices use a single electromagnet having a 3D structure, or use a permanent magnet for generating an FFL and an attached electromagnetic coil for moving the FFL. Here, in order to move the FFL or FFP in 3D space using an electromagnetic field, thousands of kW of electricity and a very complicated 3D coil are essential. Also, in order to cancel the effects of temperature and the type of MPI on the magnetic field distribution, calibration, which takes several hours to several days, is required before a sample is analyzed. That is, the conventional MPI devices have disadvantages in that the size of the device, relative to the size of a sample that can be measured through the device, is so large as to require a separate building or site therefor and in that the device consumes large amounts of power.

Documents of Related Art (Patent Document 1) Korean Patent Application Publication No. 10-2009-0060143, published on Jun. 11, 2009 and titled "Quantitative detection method of biomolecules using magnetic nano particle and frequency-mixing magnetic reader".

SUMMARY OF THE INVENTION

An object of an embodiment is to reduce the amount of power consumed for imaging the 3D distribution of a sample including nano magnetic particles.

Another object of the embodiment is to solve a problem in which it is not easy to move a magnetic-field-free region.

An apparatus for imaging nano magnetic particles according to an embodiment may include a measurement head in which a through hole for accommodating a sample including the nano magnetic particles is formed and in which an excitation coil and a detection coil are installed, a field-free region generation unit for forming a field-free region, in which there are few or no magnetic fields, in a spacing area between identical magnetic poles that face each other, and a control unit for applying a signal to the excitation coil when the measurement head is placed within the spacing area of the field-free region generation unit, controlling the field-free region so as to move in the sample, and imaging the 3D positional distribution of the nano magnetic particles included in the sample based on a detection signal output from the detection coil.

Here, the excitation coil may include a low-frequency coil and a high-frequency coil, and may generate a mixed magnetic field by mixing a first magnetic field generated in the low-frequency coil with a second magnetic field generated in the high-frequency coil.

Here, the detection coil may be a differential detection coil formed by connecting two coils wound in different directions.

Here, the field-free region may be a Field-Free Point (FFP) or a Field-Free Line (FFL).

Here, the identical magnetic poles that face each other may be formed using at least one of a permanent magnet and a direct-current (DC) coil.

Here, the permanent magnet may be a neodium magnet.

Here, the identical magnetic poles that face each other may be two pairs.

Here, the field-free region generation unit may include a hexahedral housing including an opening formed in the top surface thereof, a permanent magnet may be installed on each of the bottom surface of the housing and the two side surfaces thereof, which face each other, and a direct-current (DC) coil may be formed around the opening in the top surface.

Here, the measurement head may be inserted inside the housing by moving through the opening.

The apparatus for imaging nano magnetic particles according to an embodiment may further include a first driving unit for rotating or linearly moving the field-free region generation unit.

The apparatus for imaging nano magnetic particles according to an embodiment may further include a second driving unit for moving the measurement head to the spacing area of the field-free region generation unit.

Here, the control unit may generate a 2D image, which is the 2D positional distribution of nano magnetic particles included in the cross section of the sample, based on the detection signal, and may generate a 3D image by synthesizing multiple 2D images corresponding to multiple cross sections that are parallel to each other.

Here, after linearly moving the field-free region in one direction from the cross section of the sample, the control unit may linearly move the field-free region in another direction forming a predetermined unit angle with the one direction, may generate a sinogram using a signal that is output from the detection signal according to movement of the field-free region, and may generate the 2D image by performing inverse radon transformation on the generated sinogram.

Here, the control unit may move the measurement head by a predetermined unit length in a direction perpendicular to the cross section of the sample and repeat the generation of the 2D image.

A method for imaging nano magnetic particles according to an embodiment may include applying a signal to an excitation coil installed in a measurement head that accommodates a sample including the nano magnetic particles; and moving a field-free region, in which there are few or no magnetic fields and which is generated in a spacing area between identical magnetic poles facing each other, in a sample and imaging the 3D positional distribution of the nano magnetic particles included in the sample based on a detection signal output from the detection coil of the measurement head.

Here, the detection coil may be a differential detection coil formed by connecting two coils wound in different directions.

Here, the field-free region may be a Field-Free Point (FFP) or a Field-Free Line (FFL).

Here, the identical magnetic poles facing each other may be formed using at least one of a permanent magnet and a direct-current (DC) coil.

Here, imaging the 3D positional distribution of the nano magnetic particles may include generating a 2D image, which is the 2D positional distribution of nano magnetic particles included in the cross section of the sample, based on the detection signal and generating a 3D image by synthesizing multiple 2D images corresponding to multiple cross sections that are parallel to each other.

Here, generating the 2D image may be configured such that, after the field-free region is linearly moved in one direction from the cross section of the sample, the field-free region is linearly moved in another direction, forming a predetermined unit angle with the one direction, a sinogram is generated using a signal that is output from a detection signal according to movement of the field-free region, and the 2D image is generated by performing inverse radon transformation on the generated sinogram.

Here, generating the 2D image may be configured to move the measurement head by a predetermined unit length in a direction perpendicular to the cross section of the sample and to repeat generation of the 2D image.

BRIEF DESCRIPTION OF THE DRAWINGS

The above and other objects, features and advantages of the present invention will be more clearly understood from the following detailed description, taken in conjunction with the accompanying drawings, in which.

DESCRIPTION OF THE PREFERRED EMBODIMENTS

Figure 1:
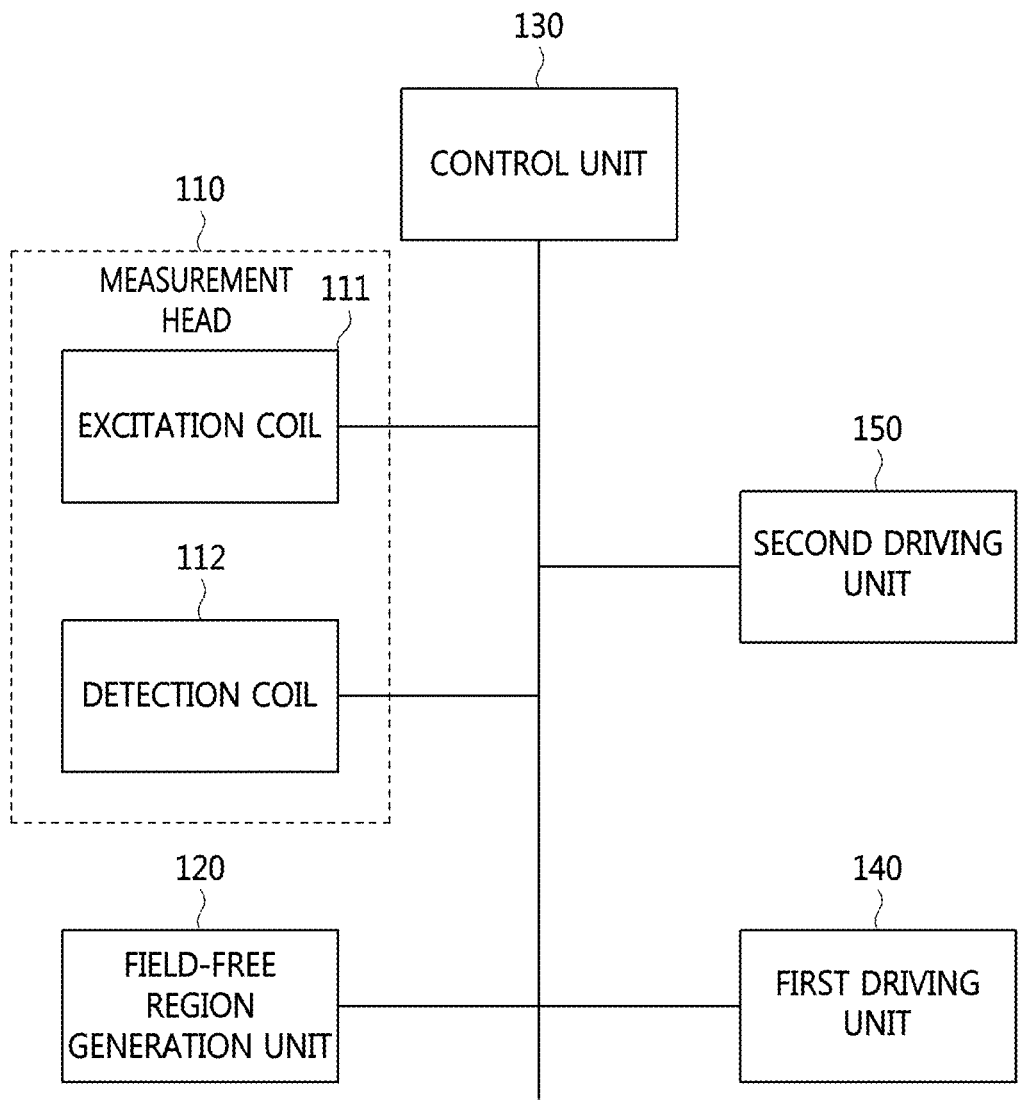
FIG. 1 is a schematic block diagram of an apparatus for imaging nano magnetic particles according to an embodiment.

The advantages and features of the present invention and methods of achieving them will be apparent from the following exemplary embodiments to be described in more detail with reference to the accompanying drawings. However, it should be noted that the present invention is not limited to the following exemplary embodiments, and may be implemented in various forms. Accordingly, the exemplary embodiments are provided only to disclose the present invention and to let those skilled in the art know the category of the present invention, and the present invention is to be defined based only on the claims. The same reference numerals or the same reference designators denote the same elements throughout the specification.

It will be understood that, although the terms "first," "second," etc. may be used herein to describe various elements, these elements are not intended to be limited by these terms. These terms are only used to distinguish one element from another element. For example, a first element discussed below could be referred to as a second element without departing from the teachings of the present invention.

The terms used herein are for the purpose of describing particular embodiments only and are not intended to limit the present invention. As used herein, the singular forms are intended to include the plural forms as well, unless the context clearly indicates otherwise. It will be further understood that the terms "comprises," "comprising,", "includes" and/or "including," when used herein, specify the presence of stated features, integers, steps, operations, elements, and/or components, but do not preclude the presence or addition of one or more other features, integers, steps, operations, elements, components, and/or groups thereof.

Unless differently defined, all terms used here, including technical or scientific terms, have the same meanings as terms generally understood by those skilled in the art to which the present invention pertains. Terms identical to those defined in generally used dictionaries should be interpreted as having meanings identical to contextual meanings of the related art, and are not to be interpreted as having ideal or excessively formal meanings unless they are definitively defined in the present specification.

Hereinafter, an apparatus and method for imaging nano magnetic particles according to an embodiment will be described in detail with reference to FIGS. 1 to 10.

Figure 2:
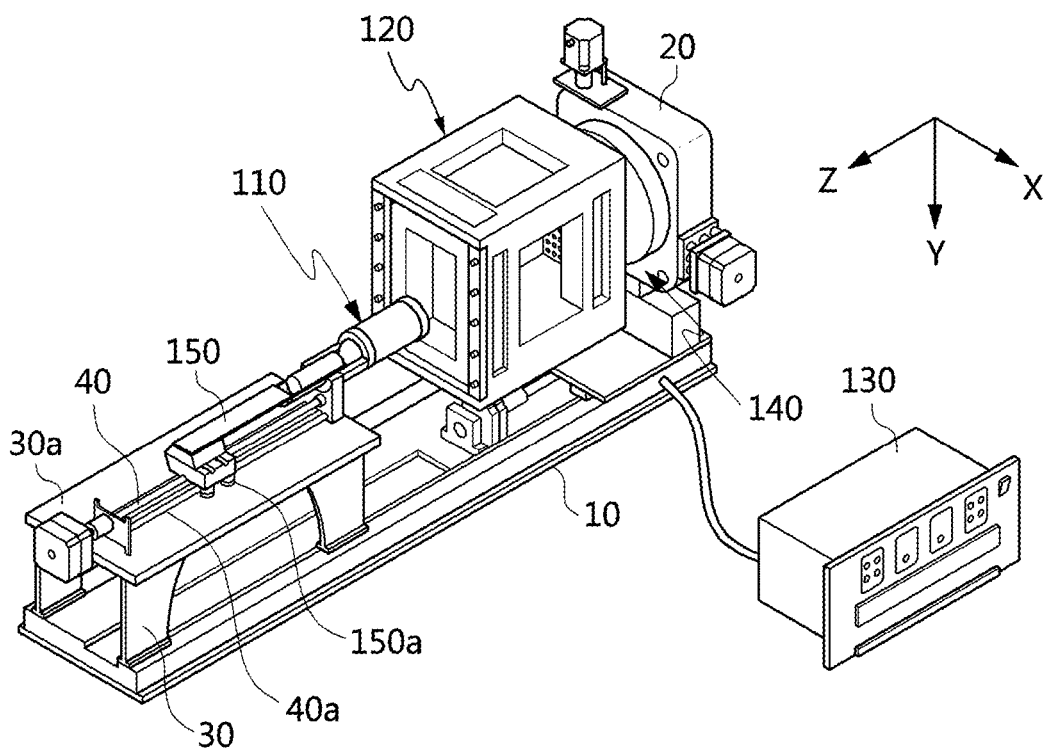
FIG. 2 is a view illustrating an example of the structure diagram of an apparatus for imaging nano magnetic particles according to an embodiment.

FIG. 1 is a schematic block diagram of an apparatus for imaging nano magnetic particles according to an embodiment, and FIG. 2 is a view illustrating an example of the structure diagram of an apparatus for imaging nano magnetic particles according to an embodiment.

Referring to FIG. 1, a nano-magnetic-particle-imaging apparatus 1 according to an embodiment includes a measurement head 110, a field-free region generation unit 120, and a control unit 130.

In the measurement head 110, a through hole in which a sample including nano magnetic particles is accommodated is formed. Also, an excitation coil 111 and a detection coil 112 are installed in the measurement head 110. Here, the excitation coil 111 generates a magnetic field in the measurement head 110, into which the sample including nano magnetic particles is inserted. Here, the detection coil 112 may acquire a detection signal from the sample placed in the through hole in the measurement head 110. The measurement head 110 will be described in detail later with reference to FIGS. 3 to 7.

The field-free region generation unit 120 forms a field-free region, in which there are few or no magnetic fields, inside a spacing area between identical magnetic poles that face each other.

Here, the basic principle of signal acquisition in Magnetic Particle Imaging (MPI) is based on a harmonic signal caused by nonlinear magnetic properties of Nano Magnetic Particles (NMP) in a gradient magnetic field. Here, two identical magnetic poles are made to face each other, which causes saturation without generation of a nonlinear magnetization phenomenon, whereby a field-free region is generated in a predetermined area of the spacing area. Additionally, the field-free region is moved in the space, and imaging is realized using the spatial location at which a harmonic signal is generated.

Here, the field-free region may be a Field-Free Point (FFP) or a Field-Free Line (FFL).

Here, the identical magnetic poles facing each other may be formed using at least one of a permanent magnet and a direct-current (DC) coil. Here, the permanent magnet may be a neodium magnet (N30 grade). Here, the identical magnetic poles facing each other may comprise two pairs.

Here, when the field-free region generation unit 120 is implemented using a permanent magnet, power for applying an electromagnetic field is not required. Also, even though the field-free region generation unit 120 is implemented using a DC coil, the amount of power that is applied is not much. Therefore, the amount of power consumed for 3D imaging of nano magnetic particles may be significantly reduced.

Meanwhile, as illustrated in FIG. 2, the field-free region generation unit 120 may be implemented such that a permanent magnet or a DC coil is mounted in a hexahedral housing in which an inner space is formed. However, the shape of the field-free region generation unit 120 illustrated in FIG. 2 is merely an embodiment, and the present invention is not limited thereto. Also, the structure of the field-free region generation unit 120 will be described in detail later with reference to FIG. 8.

The control unit 130 controls the overall process of nano magnetic particle imaging by controlling the components. Here, the control unit 130 may include any of all types of devices capable of processing data, such as a processor. Here, the term 'processor' may indicate, for example, a data-processing device embedded in hardware, which has a physically structured circuit in order to perform a function expressed using code or instructions included in a program.

According to an embodiment, when the measurement head 110 is located in the spacing area of the field-free region generation unit 120, the control unit 130 applies a signal to the excitation coil 111, performs control so as to move the field-free region within a sample, and images the 3D positional distribution of the nano magnetic particles included in the sample based on a detection signal output from the detection coil 112. According to an embodiment, the control unit 130 performs control so as to continuously move the FFP or FFL, and arranges the detection signals, which are detected when the sample overlaps the FFP or FFL, thereby acquiring 3D image information corresponding to the nano magnetic particles. For example, the 3D image information may include stereoscopic image information in the form of a contour plot.

Here, the control unit 130 may generate a 2D image, which is the 2D positional distribution of the nano magnetic particles included in the cross section of the sample, based on the detection signal, and may generate a 3D image by synthesizing multiple 2D images corresponding to multiple cross sections that are parallel to each other. Here, the cross section of the sample may, for example, be parallel to the XY plane illustrated in FIG. 2.

Here, the control unit 130 linearly moves the field-free region in one direction from the cross section of the sample and then linearly moves the field-free region in another direction that forms a predetermined unit angle with the one direction. Then, the control unit 130 generates a sinogram using a signal that is output from the detection signal according to the movement of the field-free region and performs inverse radon transformation on the generated sinogram, thereby generating a 2D image.

Here, the sinogram corresponds to projection data that is acquired from one direction and is then sequentially arranged in the projection direction. In the sinogram, the pixel values in each row match the amplitude of the corresponding profile at the corresponding position. The sinogram is well-known art, and thus a detailed description thereof will be omitted. Also, the inverse radon transform is a 2D image generation method using a sinogram, which is widely used for CT or the like. Inverse radon transform is technology published in the paper written by Kak, A. C., and M. Slaney and titled "Principles of Computerized Tomographic Imaging" (New York, N.Y., IEEE press, 1988), so a detailed description thereof will be omitted.

For example, referring to FIG. 2, the field-free region may be rotated by the predetermined unit angle from the XY plane, or may be linearly moved in the state in which the field-free region is rotated. This may be referred to as T-round stage movement.

To this end, the nano-magnetic-particle-imaging apparatus 1 according to an embodiment may further include a first driving unit 140 for rotating or linearly moving the field-free region generation unit 120.

For example, referring to FIG. 2, the apparatus 1 includes a support 20 that is formed so as to be perpendicular to a base 10 at one end thereof, and the first driving unit 140 may be joined to the upper surface of the support 20 in order to enable T-round stage movement. Accordingly, the field-free region generation unit 120 is joined to the first driving unit 140 by being fixed to the upper part thereof, whereby the field-free region generation unit 120 may be moved along with the first driving unit 140 at the time of T-round stage movement. Also, as illustrated in FIG. 2, the field-free region generation unit 120 may be installed at a location at which a predetermined spacing area between the field-free region generation unit 120 and the base 10 can be secured in order to enable T-round stage movement.

Also, the control unit 130 may move the measurement head 110 by a predetermined unit length in a direction perpendicular to the cross section of the sample, and may repeat the generation of a 2D image. That is, when the measurement head 110 is linearly moved in the Z-axis direction, 2D images for the respective cross sections through which the field-free region passes may be acquired.

To this end, the nano-magnetic-particle imaging apparatus 1 according to an embodiment may further include a second driving unit 150 for moving the measurement head 110 to the spacing area of the field-free region generation unit 120.

For example, referring to FIG. 2, the second driving unit 150 may be installed on the upper part of a rack 30 in the form of a table, which is placed at the other end of the base 10. Here, the rack 30 may be installed such that the top plate 30a thereof is placed at the position at the height of the field-free region generation unit 120 in order to enable the measurement head 110 to be inserted into the field-free region generation unit 120.

Here, a movement guide 40 having therein a groove 40a is formed on the upper part of the rack 30 so as to be parallel to the Z-axis, and an engagement part 150a, insertable in the groove 40a, may be formed in the second driving unit 150. Accordingly, under the control of the control unit 130, the second driving unit 150 moves along the movement guide 40 in the state in which the engagement part 150a thereof is fastened to the groove 40a, whereby the measurement head 110 may move along the Z-axis and enter the field-free region generation unit 120.

Also, the nano-magnetic-particle-imaging apparatus 1 according to an embodiment of the present invention may include an interface unit (not illustrated), which is able to output an image of nano magnetic particles and receive a control selection for nano-magnetic-particle imaging from a manipulator, or may be connected with the interface unit. The interface unit may include both an input function and an output function. For example, the input unit may be provided through a keyboard, a mouse, or any of various methods such as sound recognition, and the like, and the output unit may be provided through a projector, various types of display panels, sound, vibration, and the like. Also, the input unit and the output unit may be implemented in the form of a single touch panel.

Figure 3:
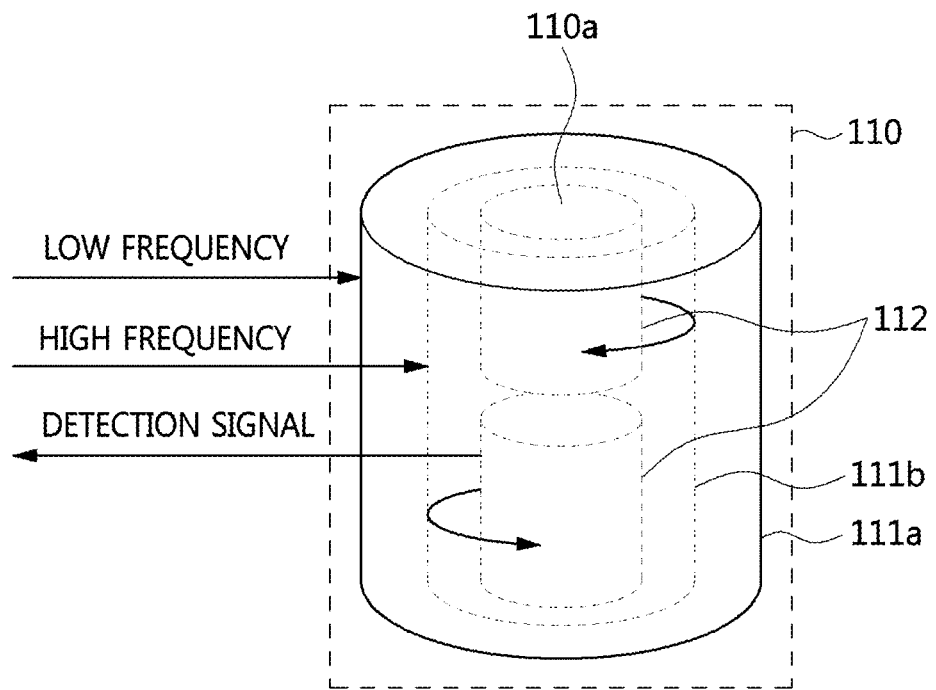
FIG. 3 is an exemplary view schematically illustrating the structure of the coil of a measurement head according to an embodiment.
Figure 4:
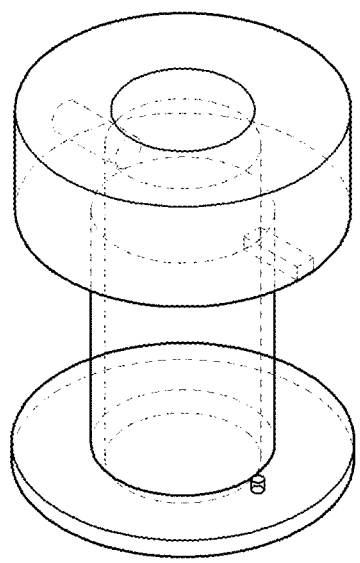
FIG. 4 is an exemplary view of a bobbin structure in the state in which an excitation coil is installed in a measurement head according to an embodiment.
Figure 5:
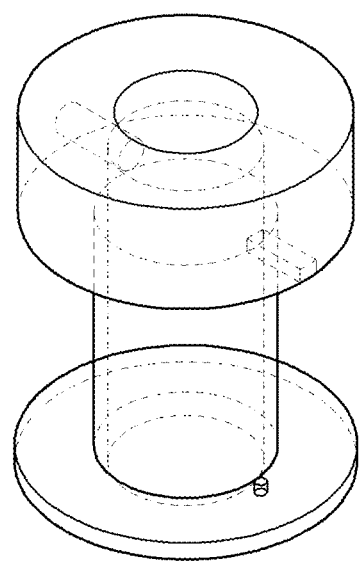
FIG. 5 is an exemplary view of a bobbin structure in the state in which a detection coil is installed in a measurement head according to an embodiment.
Figure 6:
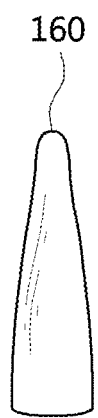
FIG. 6 is an exemplary view of a sample container according to an embodiment.
Figure 7:
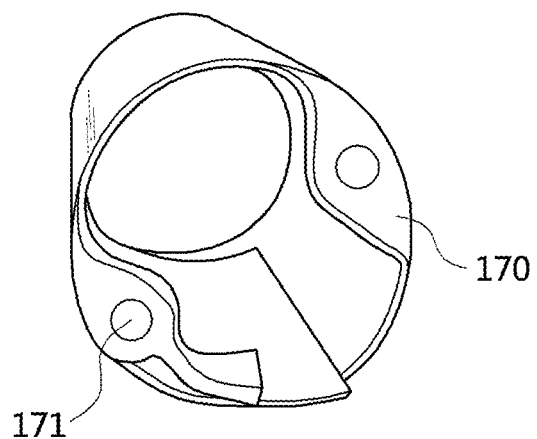
FIG. 7 is an exemplary view of a sample container holder according to an embodiment.

FIG. 3 is an exemplary view schematically illustrating the structure of a coil in a measurement head according to an embodiment, FIG. 4 is an exemplary view of a bobbin structure in the state in which an excitation coil is installed in a measurement head according to an embodiment, FIG. 5 is an exemplary view of a bobbin structure in the state in which a detection coil is installed in a measurement head according to an embodiment, FIG. 6 is an exemplary view of a sample container according to an embodiment, and FIG. 7 is an exemplary view of a sample container holder according to an embodiment.

Referring to FIG. 3, the measurement head 110 may include excitation coils 111a and 111b and a detection coil 112.

Here, each of the excitation coils 111a and 111b is a solenoid coil for generating a magnetic field, and a mixed magnetic field in which the two magnetic fields generated from the respective excitation coils are mixed may be generated.

Here, the excitation coils 111a and 111b may be a low-frequency coil 111a and a high-frequency coil 111b, respectively.

Here, the low-frequency coil 111a may be located on the outermost side of the measurement head 110, the high-frequency coil 111b may be located in the interior of the low-frequency coil 111a, and the detection coil 120 may be located in the interior of the high-frequency coil 111b. That is, the measurement head 110 includes the low-frequency coil 111a and the high-frequency coil 111b, and generates a magnetic field using a low-frequency signal and a magnetic field using a high-frequency signal, thereby generating a mixed magnetic field. Here, the process of calibrating the low-frequency coil 111a and the high-frequency coil 111b may be performed depending on the mixed magnetic field in an embodiment.

Also, the low-frequency coil 111a may receive a signal applied from a power source corresponding to a low-frequency voltage, and the high-frequency coil 111b may receive a signal applied from a power source corresponding to a high-frequency voltage.

Here, electromotive force output by the detection coil 112 may correspond to a detection signal. Here, the detection coil 112 may be a differential detection coil formed by connecting two coils that are wound in different directions. Therefore, a combination of signals detected from the two coils, which are wound in different directions, is acquired as a detection signal in the detection coil 112.

Accordingly, in order to acquire a harmonic signal on the nonlinear FFL or FFP, two different frequencies are used in the excitation coils, and simultaneously, one side of the differential coil is saturated with a strong magnetic field, whereby the situation in which signals are output from all of the opposite sides of the detection coil may be declined while maintaining the effect of differential detection.

Referring to FIG. 4, the measurement head 110 has a structure in which the high-frequency coil is wound inside and the low-frequency coil is wound outside.

Referring to FIG. 5, the detection coil has a differential coil structure in which the upper part thereof is formed by winding the coil clockwise and the lower part thereof is formed by winding the coil counterclockwise.

The detection coil of FIG. 5 is inserted into the interior of the coil of FIG. 4, whereby the signals generated from the high-frequency coil and the low-frequency coil are physically canceled and a structure in which only the signal generated from the substance located in the interior of the detection coil can be received may be realized.

Table 1 contains details about the width, the inner radius, the height, and the wire diameter of each of the detection coil, the high-frequency coil (middle HF coil), and the low-frequency coil (outer LF coil) installed in the above-described structure.

TABLE 1

|  | detection coil | middle HF coil | outer LF coil |
|---|---|---|---|
| width (mm) | 40 | 101 | 101 |
| inner radius (mm) | 21 | 26.5 | 27.5 |
| height (mm) | 1.75 | 0.81 | 3.81 |
| wire diameter (mm) | 0.3 | 0.4 | 0.4 |

Figure 8:
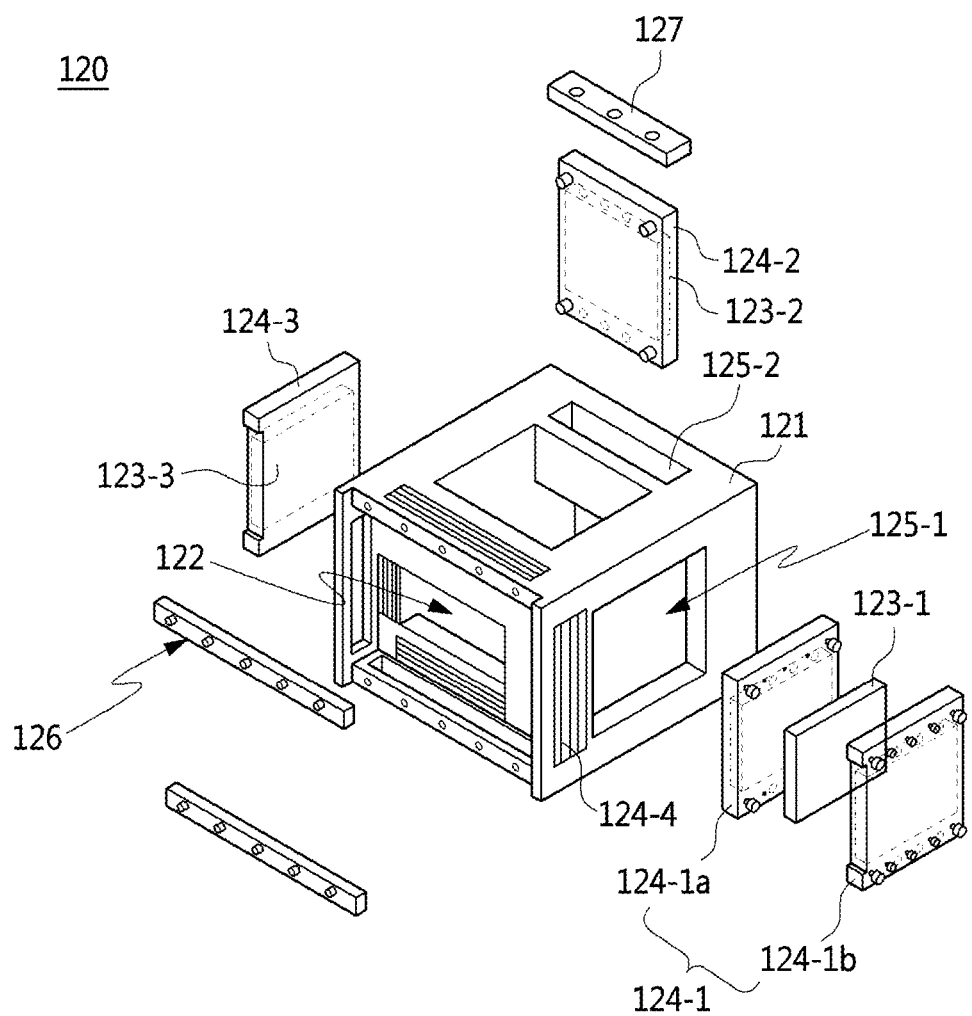
FIG. 8 is an example of a decomposition perspective view of a field-free region generation unit according to an embodiment.

Meanwhile, referring to FIG. 3, the through hole 110a is formed in the measurement head 110, and a sample including nano magnetic particles may be accommodated in the through hole 110a. Here, after the sample is inserted in a sample container 160 in the form of a PCR tube, as illustrated in FIG. 6, the sample container 160 may be fitted into the opening 171 in a plastic cylindrical sample holder 170, as illustrated in FIG. 7. Then, the sample holder 170 may be inserted into the through hole 110a of the measurement head 110. However, this is merely an example, and the present invention is not limited thereto. That is, this example is used when the sample is not solid matter. When the sample is a laboratory rat or another solid sample, the sample may be directly inserted into the through hole 110a without the sample container 160 or the sample holder 170. FIG. 8 is an example of a decomposition perspective view of a field-free region generation unit according to an embodiment.

Referring to FIG. 8, the field-free region generation unit 120 may include a hexahedral housing 121, and an opening 122 may be formed in the top surface of the housing. Accordingly, the measurement head 110 is inserted through the opening 122, whereby the measurement head 110 may be accommodated.

Here, although permanent magnets 123-1, 123-2 and 123-3 are installed on the two side surfaces of the housing 121, which face each other, and on the bottom surface thereof, a DC coil 124-4 may be installed on the top surface of the housing 121 in place of a permanent magnet, whereby the opening 122 may be formed in the top surface.

Here, the DC coil 124-4 is a solenoid coil having about 1000 turns of a coil of about 1.3 mm, and DC power may be applied thereto.

Here, special cases 124-1, 124-2 and 124-3 for accommodating the permanent magnets 123-1, 123-2 and 123-3 are provided, and the permanent magnet 123-1 may be held between two detachable covers 124-1a and 124-1b and mounted to the housing 121.

Here, grooves 125-1 and 125-2 for accommodating the permanent magnets 123-1 and 123-2 may be formed in the housing 121. Here, as illustrated in FIG. 8, a relatively wide and shallow groove 125-1 may be formed in the side surface, and a relatively narrow and deep groove 125-2 may be formed in the bottom surface.

Accordingly, the cases 124-1 and 124-2 in which the permanent magnets 123-1 and 123-2 are contained may be mounted into the grooves 125-1 and 125-2. Here, the cases 124-1 and 124-2 may be engaged with the housing 121 through screw coupling or the like.

Although an example in which the permanent magnets are installed on the two side surfaces is illustrated in FIG. 8, the permanent magnets may be installed on the other two side surfaces in another embodiment.

Here, when the permanent magnets 123-1 and 123-3 are placed such that the N poles thereof face each other, the other permanent magnet 123-2 is placed such that the S pole thereof faces the top surface of the housing, and the direction in which current is applied to the DC coil 124-4 may be controlled such that the S pole is formed to be oriented to the bottom surface of the housing.

Figure 9:
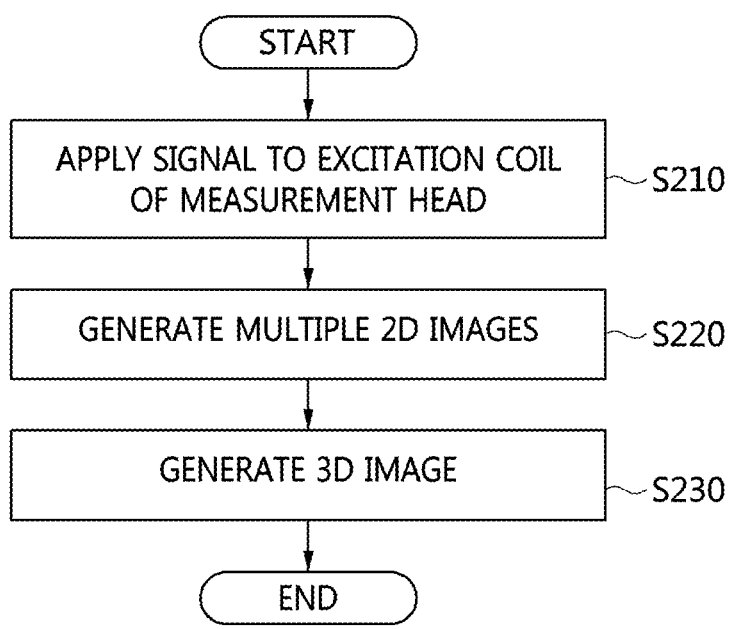
FIG. 9 is a flowchart for explaining a method for imaging magnetic particles according to an embodiment.

FIG. 9 is a flowchart for explaining a method for imaging magnetic particles according to an embodiment. Here, the method for imaging magnetic particles is performed by the apparatus for imaging magnetic particles described above with reference to FIGS. 1 to 8, and thus a repeated description will be omitted.

Referring to FIG. 9, the method for imaging nano magnetic particles according to an embodiment may include applying a signal to an excitation coil installed in a measurement head that accommodates a sample including nano magnetic particles at step S210 and imaging the 3D positional distribution of the nano magnetic particles included in the sample based on a detection signal that is output from the detection coil of the measurement head by moving a magnetic-field-free region, which is generated in a spacing area between the identical magnetic poles facing each other, in the sample at steps S220 to S230.

Here, imaging the 3D positional distribution of the nano magnetic particles may include generating a 2D image, which is the 2D positional distribution of the nano magnetic particles included in the cross section of the sample, based on the detection signal at step S220 and generating a 3D image by synthesizing multiple 2D images corresponding to multiple cross sections that are parallel to each other. Here, generating the 2D image at step S220 may be configured such that, after the field-free region is linearly moved in one direction from the cross section of the sample, the field-free region is linearly moved in another direction, which forms a predetermined unit angle with the one direction, a sinogram is generated using a signal that is output from the detection signal according to the movement of the field-free region, and inverse radon transformation is performed on the generated sinogram, whereby the 2D image may be generated. A detailed description thereof will be made later with reference to FIG. 10.

Also, the measurement head is moved by a predetermined unit length in a direction perpendicular to the cross section of the sample, and generating the 2D image at step S220 may be repeated.

Figure 10:
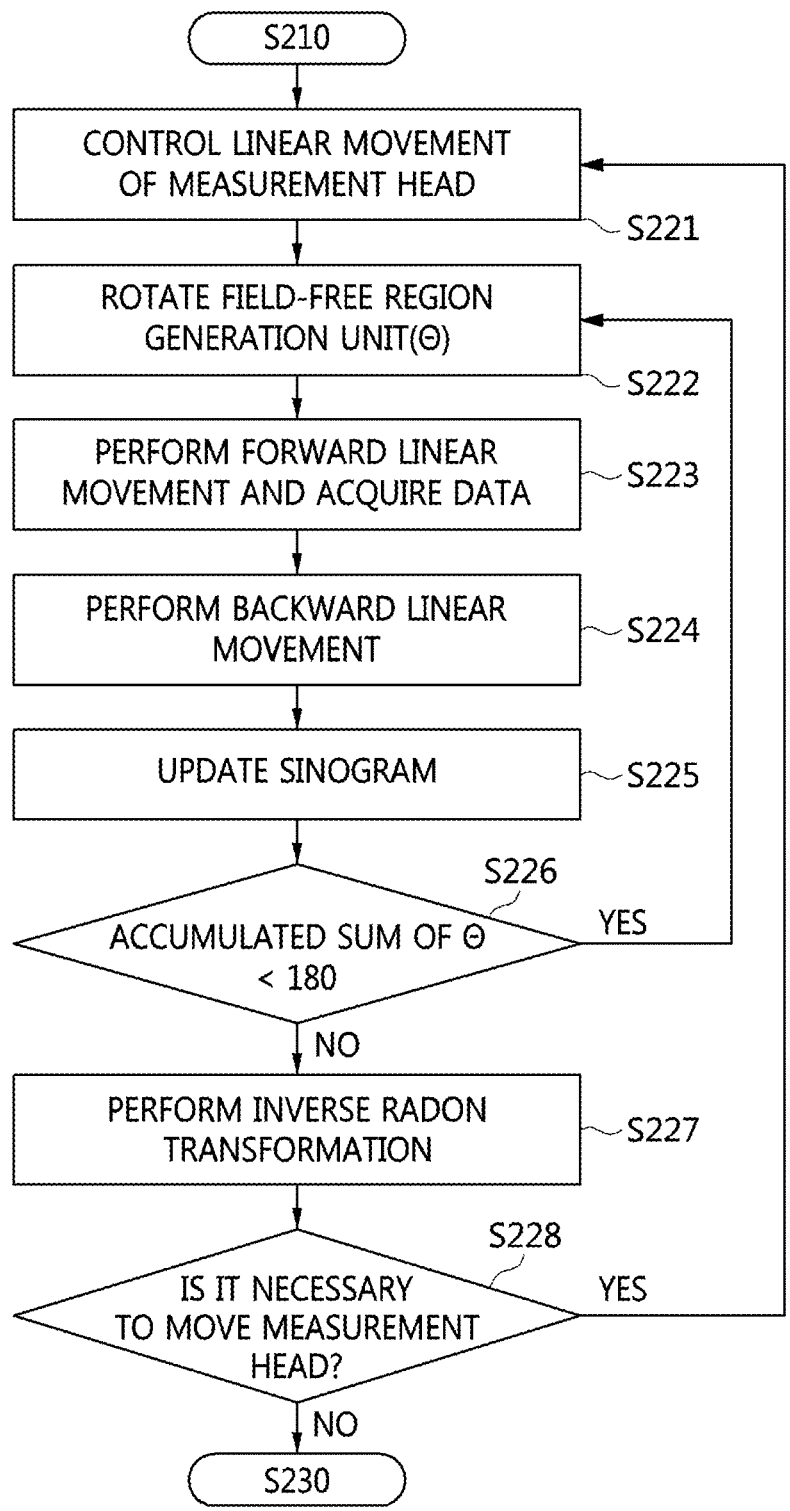
FIG. 10 is a flowchart for specifically explaining the step of generating a 2D image in FIG. 9.
Figure 11:
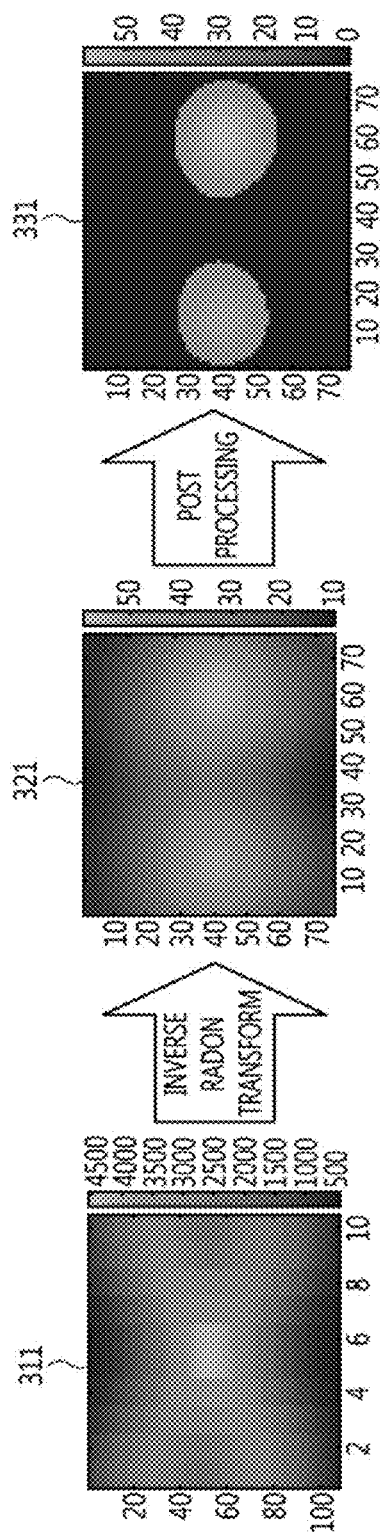
FIG. 11 is an exemplary view of a 2D image generated according to an embodiment.
Figure 12:
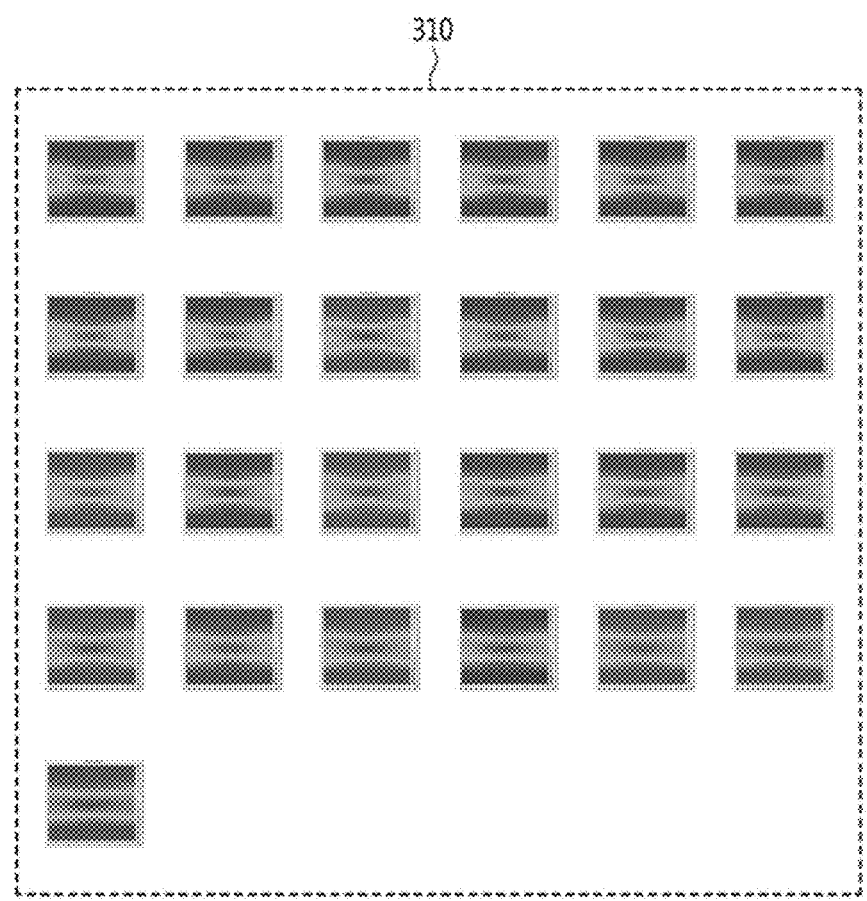
FIG. 12 is an exemplary view of multiple sinograms corresponding to multiple cross sections according to an embodiment.
Figure 13:
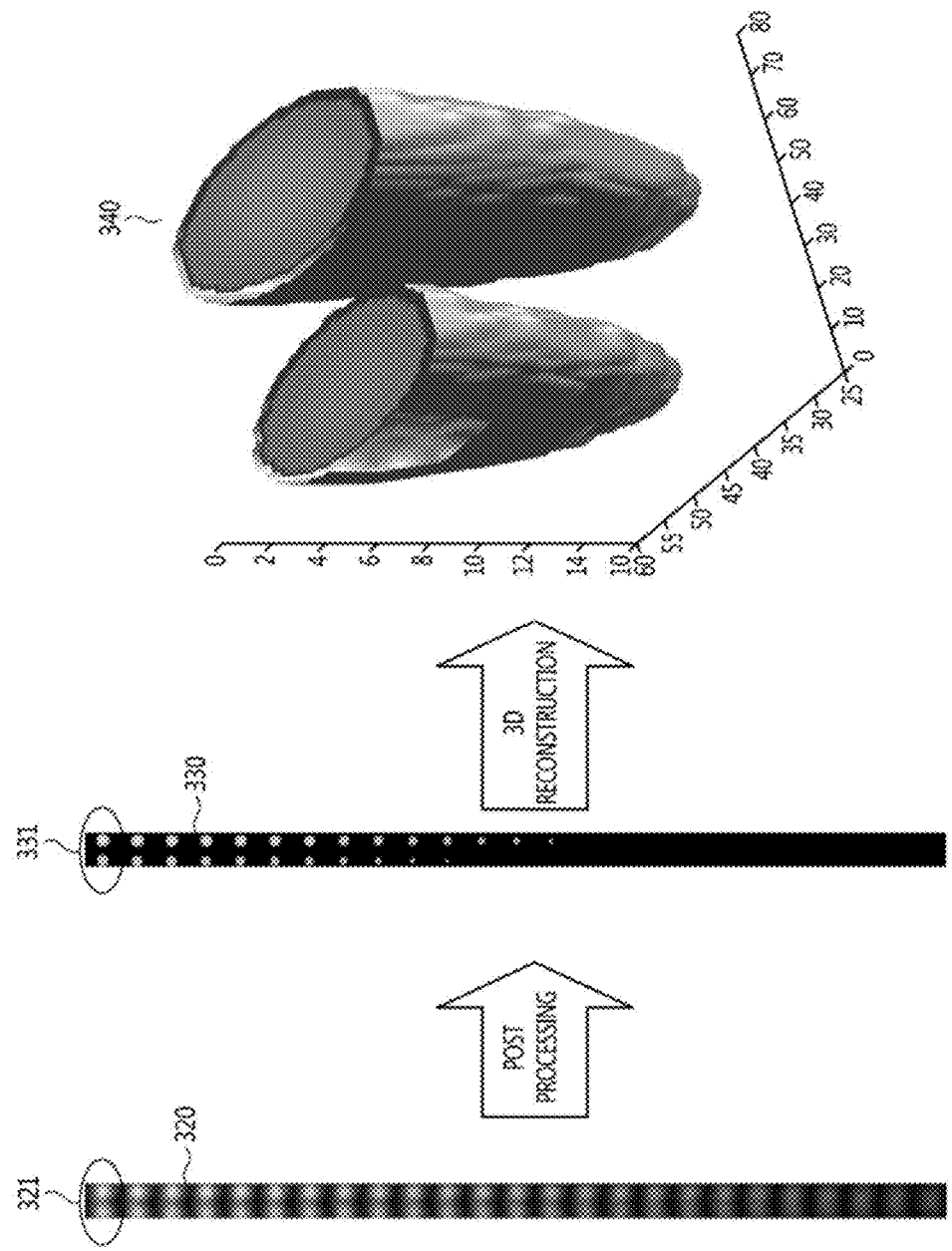
FIG. 13 is an exemplary view of an image of the 3D positional distribution of nano magnetic particles, generated according to an embodiment.

FIG. 10 is a flowchart for specifically explaining the step of generating a 2D image illustrated in FIG. 9, FIG. 11 is an exemplary view of the 2D image generated according to an embodiment, FIG. 12 is an exemplary view of multiple sinograms corresponding to multiple cross sections according to an embodiment, and FIG. 13 is an exemplary view of an image of the 3D positional distribution of nano magnetic particles, which is generated according to an embodiment.

Referring to FIG. 10, first, the control unit 130 controls the linear movement of the measurement head 110 at step S221. That is, the position of the sample on the Z-axis is adjusted. At the outset, the position is adjusted such that the FFL or FFP passes through the peak or bottom point of the sample.

Then, the control unit 130 rotates the field-free region generation unit 120 by 0 degrees, which is a predetermined angle, at step S222. That is, the FFL or FFP generated by the field-free region generation unit 120 is rotated by 0 degrees from one cross section of the sample (XY plane).

The control unit 130 continuously makes the field-free region generation unit 120 linearly move forwards and acquires a signal detected by the detection coil 112 at predetermined unit time intervals at step S223.

Then, the control unit 130 makes the field-free region generation unit 120 linearly move backwards by the distance that the field-free region generation unit 120 was linearly moved forwards, thereby returning the field-free region generation unit 120 to its original position at step S224.

Then, the control unit 130 updates a sinogram capable of representing a predetermined image signal based on the signal output from the detection coil 112 at step S225.

Then, the control unit 130 determines at step S226 whether the accumulated sum of the rotated angle θ is less than 180 degrees.

When it is determined at step S226 that the accumulated sum of the rotated angle θ is less than 180 degrees, the control unit 130 performs control so as to repeatedly perform steps S222 to S225. Conversely, when it is determined at step S226 that the accumulated sum of the rotated angle θ is not less than 180 degrees, the control unit 130 performs inverse radon transformation on the generated sinogram, thereby realizing 2D imaging of the cross section (XY plane) of the sample at the current height at step S227.

For example, referring to FIG. 11, a sinogram 311 of a predetermined cross section based on the Z-axis direction is generated through steps S222 to S226. Here, two samples at opposite sides are taken, whereby a sinogram 311 in the shape of an X is obtained.

Through step S227, a 2D image 321, which is the inverse radon transform of the sinogram 311, is generated. However, when the 2D image 321 is blurry, as shown in FIG. 11, a more clear 2D image 331 may be generated by performing postprocessing. Here, the postprocessing may be making only the images within a predetermined distance from the center of the two samples on the 2D image 321 appear, or processing the signals so as to save only signals having a strength equal to or greater than a predetermined threshold.

Then, the control unit 130 determines at step S228 whether it is necessary to linearly move the measurement head 110. That is, when the measurement head starts to move after the FFL passes through the peak point of the sample, whether the FFL reaches the bottom point thereof is determined, or when the measurement head starts to move after the FFL passes through the bottom point of the sample, whether the FFL reaches the peak point thereof is determined.

When it is determined at step S228 that it is necessary to linearly move the measurement head 110, the control unit 130 performs control so as to repeatedly perform steps S221 to S227. Conversely, when it is determined at step S228 that it is not necessary to linearly move the measurement head 110, the above-described step S230 is performed.

That is, multiple sinograms 310 corresponding to the multiple cross sections, which are parallel to each other, are generated by repeatedly performing steps S221 to S227, as illustrated in FIG. 12. Then, multiple 2D images 320, which are inverse radon transform of the multiple sinograms 310, are generated, as illustrated in FIG. 13. As described above, postprocessing is additionally performed on the multiple 2D images 320, whereby 2D images 330 may be generated. Observing the 2D images 320 and 330, a signal becomes weaker approaching the lower side based on the Z-axis. This is because the sample has a conical shape.

The multiple 2D images 330 are synthesized at step S230, whereby a 3D image 340 for the two samples, each having a conical shape, may be generated.

According to an embodiment, imaging the 3D distribution of a specific sample may be realized by forming a magnetic field using only the power applied to an excitation coil. Therefore, power consumption may be reduced, and an FFL or FFP may be freely moved.

Although the embodiments of the present invention have been described with reference to the accompanying drawings, those skilled in the art will appreciate that the present invention may be practiced in other specific forms without changing the technical sprit or essential features of the present invention. Therefore, the embodiments described above are illustrative in all aspects and should not be understood as limiting the present invention.

What is claimed is:

1. An apparatus for imaging nano magnetic particles, comprising:
    a measurement head in which a through hole for accommodating a sample including the nano magnetic particles is formed and in which an excitation coil and a detection coil are installed;
    a field-free region generation unit for forming a field-free region, in which there are few or no magnetic fields, in a spacing area between identical magnetic poles that face each other; and
    a control unit for applying a signal to the excitation coil when the measurement head is placed within the spacing area of the field-free region generation unit, controlling the field-free region so as to move in the sample, and imaging 3D positional distribution of the nano magnetic particles included in the sample based on a detection signal output from the detection coil,
    wherein the control unit generates a 2D image, which is 2D positional distribution of nano magnetic particles included in a cross section of the sample, based on the detection signal, and generates a 3D image by synthesizing multiple 2D images corresponding to multiple cross sections that are parallel to each other, and
    wherein, after linearly moving the field-free region in one direction from the cross section of the sample, the control unit linearly moves the field-free region in another direction forming a predetermined unit angle with the one direction, generates a sinogram using a signal that is output from the detection signal according to movement of the field-free region, and generates the 2D image by performing inverse radon transformation on the generated sinogram.

2. The apparatus of claim 1, wherein the excitation coil includes a low-frequency coil and a high-frequency coil and generates a mixed magnetic field by mixing a first magnetic field generated in the low-frequency coil with a second magnetic field generated in the high-frequency coil.

3. The apparatus of claim 1, wherein the detection coil is a differential detection coil formed by connecting two coils wound in different directions.

4. The apparatus of claim 1, wherein the field-free region is a Field-Free Point (FFP) or a Field-Free Line (FFL).

5. The apparatus of claim 1, wherein the identical magnetic poles that face each other are formed using at least one of a permanent magnet and a direct-current (DC) coil.

6. The apparatus of claim 5, wherein the permanent magnet is a neodium magnet.

7. The apparatus of claim 1, wherein the identical magnetic poles that face each other are two pairs.

8. The apparatus of claim 1, wherein:
    the field-free region generation unit includes a hexahedral housing including an opening formed in a top surface thereof,
    a permanent magnet is installed on each of a bottom surface of the housing and two side surfaces thereof, which face each other,
    a direct-current (DC) coil is formed around the opening in the top surface, and
    the measurement head is inserted inside the housing by moving through the opening.

9. The apparatus of claim 1, further comprising:
a first driving unit for rotating or linearly moving the field-free region generation unit.

10. The apparatus of claim 1, further comprising:
a second driving unit for moving the measurement head to the spacing area of the field-free region generation unit.

11. The apparatus of claim 1, wherein the measurement head is moved by a predetermined unit length in a direction perpendicular to the cross section of the sample and generation of the 2D image is repeated.

12. A method for imaging nano magnetic particles, comprising:
applying a signal to an excitation coil installed in a measurement head that accommodates a sample including the nano magnetic particles; and
moving a field-free region, in which there are few or no magnetic fields and which is generated in a spacing area between identical magnetic poles facing each other, in a sample, and imaging 3D positional distribution of the nano magnetic particles included in the sample based on a detection signal output from a detection coil of the measurement head,
wherein imaging the 3D positional distribution of the nano magnetic particles comprises:
generating a 2D image, which is 2D positional distribution of nano magnetic particles included in a cross section of the sample, based on the detection signal; and
generating a 3D image by synthesizing multiple 2D images corresponding to multiple cross sections that are parallel to each other,
wherein generating the 2D image is configured such that, after the field-free region is linearly moved in one direction from a cross section of the sample, the field-free region is linearly moved in another direction, forming a predetermined unit angle with the one direction, a sinogram is generated using a signal that is output from a detection signal according to movement of the field-free region, and the 2D image is generated by performing inverse radon transformation on the generated sinogram.

13. The method of claim 12, wherein the detection coil is a differential detection coil formed by connecting two coils wound in different directions.

14. The method of claim 12, wherein the field-free region is a Field-Free Point (FFP) or a Field-Free Line (FFL).

15. The method of claim 12, wherein the identical magnetic poles facing each other are formed using at least one of a permanent magnet and a direct-current (DC) coil.

16. The method of claim 14, wherein generating the 2D image is configured to move the measurement head by a predetermined unit length in a direction perpendicular to a cross section of the sample and to repeat generation of the 2D image.

* * * * *